United States Patent
Van Egmond (10) Patent No.: US 6,864,401 B2
(45) Date of Patent: Mar. 8, 2005

(54) HEAT-INTEGRATED HIGH PRESSURE SYSTEM FOR SEPARATION OF BYPRODUCTS FROM AN OLEFIN STREAM

(75) Inventor: Cor Van Egmond, Pasadena, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 212 days.

(21) Appl. No.: 10/207,414

(22) Filed: Jul. 29, 2002

(65) Prior Publication Data
US 2004/0019246 A1 Jan. 29, 2004

(51) Int. Cl.[7] .............................. C07C 1/00; C07C 1/24; C07C 7/04
(52) U.S. Cl. ........................ 585/639; 585/639; 585/640; 585/809
(58) Field of Search ................................. 585/638, 639, 585/640, 804

(56) References Cited

U.S. PATENT DOCUMENTS

| | | | |
|---|---|---|---|
| 4,474,647 A | 10/1984 | Asselineau et al. | 203/49 |
| 4,560,537 A | 12/1985 | Tabk | 422/190 |
| 5,090,977 A | 2/1992 | Strack et al. | 62/23 |
| 6,121,504 A | 9/2000 | Kuechler et al. | 585/640 |
| 6,403,854 B1 | 6/2002 | Miller et al. | 585/638 |
| 2002/0087041 A1 | 7/2002 | Kuechler et al. | 585/638 |

FOREIGN PATENT DOCUMENTS

| | | | |
|---|---|---|---|
| EP | 0 060 103 | 4/1985 | C07C/1/20 |
| WO | WO 02/00579 | 3/2002 | C07C/11/02 |

Primary Examiner—Walter D. Griffin
Assistant Examiner—Tam M. Nguyen
(74) Attorney, Agent, or Firm—Jaimes Sher (57) ABSTRACT

The present invention is a heat-integrated process for obtaining an ethylene and propylene enriched stream from an oxygenate to olefin reactor. The process comprises providing an effluent stream from an oxygenate to olefins reactor. The effluent stream comprises ethylene, propylene and one or more byproducts selected from the group consisting of propane, methyl acetylene, propadiene, dimethyl ether, acetaldyhyde and butylene. The process further includes quenching the effluent stream with the quench medium to provide an olefin stream. The olefin stream is separated into a heavy fraction and a remaining fraction. The remaining fraction is directed to a distillation column which separates the remaining fraction into a first fraction comprising a majority of both ethylene and a propylene and a second fraction comprising at least a majority of one or more heavier fraction. The bottoms of the distillation column is reboiled by the quench medium. The separation step allows the bottoms of the distillation column to be reboiled at a lower temperature.

38 Claims, 2 Drawing Sheets

HEAT-INTEGRATED HIGH PRESSURE SYSTEM FOR SEPARATION OF BYPRODUCTS FROM AN OLEFIN STREAM

FIELD OF THE INVENTION

This invention is directed to a heat-integrated system and process for removing oxygenates and other byproducts from an olefin stream. In particular, this invention is directed to a heat-integrated process for removing propane, dimethyl ether, MAPD, acetaledehyde or other byproducts from an ethylene and/or propylene containing stream.

BACKGROUND OF THE INVENTION

Olefins, particularly $C_2$ and $C_3$ olefins, are desirable as a feedstock for making derivative products such as oligomers, e.g., higher olefins, and polymers such as polyethylene and polypropylene. Traditionally, olefin feedstock was produced by cracking petroleum feedstock. An olefin plant has at least two parts. The reactor section makes the olefins. The recovery section recovers the desired olefins and removes impurities. The object of the recovery section is to recover olefins that meet the proper grade specification in the most efficient way.

U.S. Pat. No. 5,090,977 discloses a process for making olefins by steam cracking. The process includes separating the olefin product into methane, hydrogen, ethane, ethylene, propylene and $C_5+$ streams. The disclosed separation preferentially produces propylene. No propane, butane, butylene, or butadiene streams are produced.

Use of an oxygenate feedstock is becoming an alternative to petroleum feedstock for making olefins, particularly large quantities of ethylene and propylene for the production of higher olefins and plastic materials. In general, the olefins are formed by contacting the oxygenate components with a molecular sieve catalyst to convert oxygenates to olefins. The oxygenate-to-olefin process also needs a recovery section to separate the desired olefins from byproducts. The separation process of an oxygenate-to-olefin process needs to take into account the unique composition of the oxygenate-to-olefin reactor effluent.

U.S. Pat. No. 6,121,504 discloses a process for making olefin product from oxygenate feedstock using molecular sieve catalysts. Water and some unwanted byproducts are removed from the olefin product by contacting with a quench medium. After contacting with the quench medium, an olefin product fraction is obtained which comprises the desired olefins, but also includes dimethyl ether, methane, CO, $CO_2$, ethane, propane, and other components such as water and unreacted oxygenate feedstock. The methanol feed is reboiled by the quench medium. However, there is no discussion of alternative ways of using heat from the quench bottoms.

U.S. Pat. No. 4,474,647 discloses that dimethyl ether can adversely impact the oligomerization of certain olefins. The patent describes a process for removing dimethyl ether from a $C_4$ and/or $C_5$ olefin stream using distillation. The stream is distilled and separated into an overhead and a bottoms stream. The overhead stream contains dimethyl ether, water, and various hydrocarbons, and the bottoms stream contains purified olefins.

Eng et al., "Integration of the UOP/HYDRO MTO Process into Ethylene Plants, " 10th Ethylene Producers' Conference, 1998, disclose a de-ethanizer first flow scheme process. The flow diagram discloses a quench tower and an oxygenate removal unit. However, there is no discussion of how heat is used from the quench. EP-B1-0 060 103 discloses a process for extracting dimethyl ether from a vapor stream containing ethylene and propylene using a methanol wash system. The methanol wash removes a substantial amount of the dimethyl ether, but also removes a significant amount of the ethylene and propylene. This patent likewise does not disclose how the heat can be used more efficiently.

U.S. Pat. No. 6,403,854 discloses a method for heating the reboiler from a propane/propylene splitter with water from a quench tower in the recovery section of an oxygenate to olefin reactor. The propane/propylene splitter is located after all the oxygenates are removed from the effluent stream.

Additional methods of removing undesirable components from olefin streams are sought. In particular, it is desirable to have better methods for removing byproducts such as propane, dimethyl ether, methyl acetylene, propadiene, acetaldehyde and other byproducts without a significant loss of olefin product. It would also be better if the resulting process was heat-integrated to maximize efficiency. The present invention satisfies these and other needs.

SUMMARY OF THE INVENTION

The present invention is a heat-integrated process for obtaining an ethylene and propylene enriched stream from an oxygenate to olefin reactor. The process comprises providing an effluent stream from an oxygenate to olefins reactor. The effluent stream comprises ethylene, propylene and one or more byproduct selected from a group consisting of propane, methyl acetylene, propadiene, dimethyl ether, acetaldyhyde and butylene. The process further includes quenching the effluent stream with a quench medium to provide an olefin stream. The olefin stream is separated into a heavy fraction comprising C5+ olefins and a remaining fraction. The remaining fraction is fractionated in a distillation column having a reboiler to provide a first fraction and a second fraction. The first fraction comprises a majority of a first compound selected from a group consisting of ethylene and propylene and a second fraction comprising a majority of a second compound selected from a group consisting of dimethyl ether, propadiene, methyl acetylene, and acetaldehyde. According to this process, the reboiler is heated by the quench medium. Finally, the first fraction is substantially dried to produce an ethylene and propylene enriched stream. The process of an embodiment of the invention integrates heat from the quench tower to the reboiler of the distillation column providing an alternate use of heat. Particularly, the step of separation removes the heavy fraction comprising C5+ olefins, which provides a remaining fraction. When the remaining fraction is stripped or distilled, the bottoms temperature of the subsequent fractionation step is lower than it would have been if the feed to that fractionation step had comprised the remaining fraction and the heavy fraction. The lower temperature of the distillation column bottoms results in a greater temperature differential between the quench medium and the bottoms temperature of the distillation column. The higher temperature differential allows heat from the quench medium to be transferred to the distillation column bottoms rather than producing steam to provide reboiler heat.

According to one embodiment, the quench medium has a temperature ranging from about 95° C. to about 120° C., preferably ranging from about 100° C. to about 115° C., preferably ranging from about 102° C. to about 110° C., preferably ranging from about 105° C. to about 110° C.

According to another embodiment, the temperature of the quench medium is defined as a first temperature measured at the outlet of the quench. The temperature of the distillation column bottoms measured at the outlet of the distillation column bottoms is defined as the second temperature. The distillation columns bottoms and the quench medium are fed into a heat exchanger so that heat from the quench medium will re-boil the distillation column bottoms. The difference between the first temperature and the second temperature is at least about 2° C., 5° C., or 10° C.; preferably at least about 15° C.; more preferably at least about 20° C.

According to yet another embodiment, the effluent stream contains from 50 wt % to 95 wt % ethylene and propylene excluding water. In still another embodiment, the effluent stream contains from 25 wt % to 75 wt % ethylene excluding water. The effluent stream contains from 25 wt % to 75 wt % propylene excluding water.

The effluent stream comprises from about 5 wt % to about 25 wt % components excluding water having a boiling point lower than or equal to that of dimethyl ether according to one embodiment. According to another embodiment, the effluent stream preferably comprises from about 10 wt % to about 20 wt %, more preferably from about 12 wt % to about 17 wt % components having a boiling point lower than or equal to that of dimethyl ether, excluding water.

The heavy fraction optionally comprises at least 25% of all components having a boiling point that is lower than or equal to the boiling point of pentene. Preferably at least 35%, more preferably at least 45%; most preferably at least a majority; desirably at least 60% of all components have a boiling point that is greater than or equal to that of pentene are in the heavy fraction. In yet another embodiment, the heavy fraction optionally comprises at least 70% of all components having a boiling point that is lower than or equal to the boiling point of pentene. Preferably at least 80%, more preferably at least 90%; even more preferably 95%; most preferably from 98% to 100% of all components have a boiling point that is greater than or equal to that of pentene are in the heavy fraction.

According to one embodiment, the temperature of heavy fraction leaving the reboiler ranges from 65° C. to 125° C., more preferably from 100° C. to 125° C., even more preferably from 115° C. to 125° C., and most preferably 120° C.

According to one embodiment, no more than about 10 wt % of the total weight of propylene and ethylene is present in the heavy fraction. According to another embodiment, no more than 5 wt %, preferably no more than 2 wt %, more preferably no more than 1 wt % and most preferably no more than 0.5 wt % of the total weight of propylene and ethylene is present in the heavy fraction.

According to one embodiment, separation step is done in a condensate stripper. According to one embodiment, the fractionating step is done with a first distillation column and the separating step is done with a second distillation column.

In another embodiment, the portion of the olefin stream entering the distillation column further contains water in an amount not greater than about 15,000 wppm. According to an embodiment, from 10 to 5,000 wppm of water enters the distillation column. In another embodiment, the distillation column has an inlet pressure ranging from about 200 psig (1400 kPa) to about 290 psig (2000 kPa). According to another embodiment, the inlet pressure ranges from about 250 psig (1700 kPa) to about 290 psig (2000 kPa). In yet another embodiment, water absorbent is added to the distillation column.

In another embodiment, at least about 500 wppm of dimethyl ether enters the distillation column. In yet anther embodiment, the portion of the olefin stream entering the distillation column contains not greater than about 50 wt % dimethyl ether.

In another embodiment, the process includes separating the ethylene from the propylene in the first fraction and polymerizing the ethylene. In an embodiment, the process further comprises separating the ethylene from the propylene in the first fraction and polymerizing the propylene.

This invention will be better understood with reference to the Detailed Description of the Invention together with the drawings, which are intended to illustrate specific embodiments within the overall scope of the invention as claimed and are not provided by way of limitation of the claimed invention.

DETAILED DESCRIPTION OF THE INVENTION

The present invention is a heat-integrated process for obtaining an ethylene and propylene enriched stream from an oxygenate to olefins reactor. The process comprises providing an effluent stream from an oxygenate to olefins reactor. The effluent stream comprises ethylene, propylene and one or more byproducts selected from the group consisting of propane, methyl acetylene, propadiene, dimethyl ether, acetaldyhyde and butylene. The process further includes quenching the effluent stream with the quench medium to provide an olefin stream. The olefin stream is separated into a heavy fraction comprising C5+ olefins and a remaining fraction.

The remaining fraction is fractionated in a distillation column having a reboiler to provide a first fraction and a second fraction. The first fraction comprises a majority of a first compound selected from the group consisting of ethylene and propylene and a second fraction comprising a majority of a second compound selected from the group consisting of dimethyl ether, propadiene, methyl acetylene, and acetaldehyde. According to the process of one embodiment of the invention, the reboiler is heated by the quench medium. Finally, the first fraction is substantially dried to produce an ethylene and propylene enriched stream.

As used herein, "heavy fraction" is the bottoms fraction produced in a boiling point separation such as a distillation column or a condensate stripper.

"Remaining fraction" is a fraction of the olefin stream that remains after a heavy fraction, as defined above, is removed.

"Majority, " as it relates to a particular component, is defined as greater than 50% of that component.

As used herein, the term "byproducts" as it relates to an oxygenate-to-olefin effluent stream refers to any component that is produced in the oxygenate-to-olefin reaction other than water, ethylene, propylene and butylene. Particularly, byproducts include but are not necessarily limited to dimethyl ether, propane, carbon dioxide, methane, carbon monoxide, acetaldehyde, ethane, butane, C5+ hydrocarbons, and C5+ oxygenated hydrocarbons.

The Oxygenate-to-Olefin Reaction

Although the olefin stream can come from any conventional source, the invention is particularly suited to removing byproducts that come from the effluent product stream of an oxygenate-to-olefin process. In one embodiment of this invention, an effluent stream containing dimethyl ether is obtained by contacting oxygenate feedstock with a molecular sieve catalyst.

In one embodiment of the process of the invention, the oxygenate feedstock contains one or more oxygenates, more specifically, one or more organic compound(s) containing at least one oxygen atom. In one embodiment of the invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In one embodiment, the feedstock is selected from one or more of methanol, ethanol, dimethyl ether, diethyl ether or a combination thereof, more preferably methanol and dimethyl ether, and most preferably methanol.

The feedstock, in one embodiment, contains one or more diluent(s), typically used to reduce the concentration of the feedstock, and are generally inert under reaction conditions. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. Particularly preferred diluents are water and nitrogen, with water being particularly preferred.

The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentene, and other hydrocarbons having 4 or more carbon atoms, or mixtures thereof.

Molecular sieves capable of converting an oxygenate to an olefin compound include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves of one embodiment, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B.V., Amsterdam, Netherlands (2001).

The small, medium and large pore molecular sieves have from a 4-ring to a 12-ring or greater framework-type. In a preferred embodiment, the molecular sieves have 8-, 10- or 12-ring structures or larger and an average pore size in the range of from about 3 Å to 15 Å. In another preferred embodiment, the molecular sieves of the invention, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. No. 4,824, 554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves used in the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

In one embodiment, the molecular sieves used in the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G.M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 μm to about 0.6 μm with a D90 particle size distribution of less than about 1 μm.

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system. The reactor system preferably is a fluid bed reactor system having a first reaction zone within one or more riser reactor (s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstock is preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1,000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, is not critical. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting oxygenates to olefins using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the processes for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is a Group IIIA or VIII element from the Periodic Table of Elements) molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

According to one embodiment, the conversion of the primary oxygenate, e.g., methanol, is from 90 wt % to 98 wt %. According to another embodiment the conversion of methanol is from 92 wt % to 98 wt %, preferably from 94 wt % to 98 wt %.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt %; preferably from 98.2 wt % to 99 wt %.

Composition of the Effluent Product Stream

The effluent includes product such as ethylene, propylene, and butylene. Also present is water and unreacted methanol. Byproducts include but are not limited to methane, carbon monoxide, carbon dioxide, ethane, propane, n-butane, isooctane, ethanol, dimethyl ether, acetone, methyl acetylene, propadiene, and acetylene, as well as various esters, ketones and acids described below.

In another embodiment, the effluent stream, excluding water, comprises at least about 25 wt % ethylene. Preferably, the effluent stream, excluding water comprises from about 25 wt % ethylene to about 75 wt % ethylene, more preferably from about 30 wt % to about 60 wt %, and most preferably from about 35 wt % to about 50 wt % propylene.

In another embodiment, the effluent stream, excluding water, comprises at least about 20 wt % propylene. Preferably, the effluent stream, excluding water, comprises from about 20 wt % propylene to about 70 wt % propylene, more preferably from about 25 wt % to about 50 wt % propylene, and most preferably from about 30 wt % to about 40 wt % propylene.

It is desirable that the effluent stream, excluding water, contains a relatively low concentration of ethane, preferably a lower concentration of ethane than propane. Preferably, the effluent stream, excluding water comprises not greater than about 4 wt % ethane, more preferably not greater than about 3 wt % ethane, and most preferably not greater than about 2 wt % ethane.

It is also desirable that the effluent stream, excluding water, contain a relatively low concentration of propane. Preferably, the effluent stream, excluding water, comprises not greater than about 5 wt % propane, more preferably not greater than about 4 wt % propane, and most preferably not greater than about 3 wt % propane.

In another embodiment of the invention, the effluent stream, excluding water contains both ethylene and propylene. Desirably, the effluent stream, excluding water, contains at least about 50 wt % ethylene and propylene. Preferably, the effluent stream, excluding water, contains from about 50 wt % to about 95 wt % ethylene and propylene, more preferably from about 55 wt % to about 90 wt % ethylene and propylene, and most preferably from about 60 wt % to about 85 wt % ethylene and propylene.

The effluent of the OTO reactor stream of one embodiment contains some oxygenated hydrocarbons, including any non-reacted oxygenated feed. Furthermore, oxygenated hydrocarbons that are byproducts of the oxygenate to olefin reaction remains in the effluent stream. According to one embodiment, the amount of oxygenated hydrocarbons in the effluent stream range from about 0.2 wt % to about 30 wt % of the effluent stream excluding water.

The oxygenate hydrocarbons of this invention comprises at least one organic compound that contains at least one oxygen atom, such as aliphatic alcohols, ethers, carbonyl compounds (aldehydes, ketones, carboxylic acids, carbonates, esters and the like). In embodiments where the oxygenate hydrocarbon is an alcohol, the alcohol optionally includes an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenated hydrocarbons include, but are not limited to: alcohols such as methanol, ethanol, n-propanol, isopropanol, and $C_4$–$C_{20}$ alcohols; ethers such as methyl ethyl ether, dimethyl ether, diethyl ether, di-isopropyl ether; and other oxygenates such as formaldehyde, dimethyl carbonate, dimethyl ketone, and acetic acid. According to another embodiment, the composition comprises mixtures of all the foregoing oxygenates in various proportions.

According to one embodiment, the amount of byproducts in the effluent stream is about 25 wt % or less excluding water. According to another embodiment, the amount of byproducts in the effluent stream is from about 4 wt % to about 25 wt %, in yet another embodiment, from about 5 wt % to about 20 wt %, excluding water.

The provided effluent stream from an oxygenate-to-olefin reaction contains a large quantity of water vapor along with olefin products and other byproducts. According to one embodiment, the effluent stream from the OTO reactor contains about 25 wt % or more water. In another embodiment, it contains from about 40 wt % to about 80 wt % water, and in yet another embodiment, it contains from about 50 wt % to about 65 wt % water.

Product Quench

As noted, the oxygenate-to-olefin process forms a substantial amount of water as a byproduct. A substantial amount of water can be removed from the effluent by a quench device. A "quench device" is a device for removing a portion of the effluent stream by establishing a sufficient quantity of a liquid phase in contact with the effluent stream which condenses at least a portion of the material in the effluent stream. One example of a quench device in an oxygenateo-olefin product stream is found in U.S. Pat. No. 6,121,504 (direct product quench). The liquid matter that contacts the effluent stream and causes the condensation is called a "quench medium."

In a quench device, at least a portion of the gaseous effluent stream is rapidly condensed through contact with a quench medium in the liquid state (a form of what is typically called "direct contact heat transfer"). In one embodiment, about 10 wt % or more of the effluent stream is condensed during quenching. In another embodiment about 25 wt % or more of effluent stream is condensed during quenching. In yet another embodiment, about 50 wt % or more of the effluent stream is condensed during quenching; and in still another embodiment about 55 wt % or more of the effluent stream is condensed during quenching. According to another embodiment, at least 10 wt % of the water in the effluent stream is condensed during quenching. In another embodiment about 50 wt % or more of the water in the effluent stream is condensed during quenching. In yet another embodiment about 75 wt % or more, and in still another embodiment about 95 wt % or more of the water in the effluent stream is condensed during quenching. When quenching in a quench device, at least a portion of the prime olefins in a gaseous state are separated from the condensed components of the gaseous effluent stream.

In one aspect of the present invention, the pressure within a solids wash device, including a quench device, is less than 50 psi (345 kPa) below the pressure at which the effluent stream leaves the OTO reactor and no less than atmospheric pressure. In another aspect, the pressure within the solids wash device, including the quench device, is less than 50 psi (345 kPa) below the pressure at which the effluent stream leaves the OTO reactor and above atmospheric pressure, in yet another aspect it is less than 25 psi (172 kPa) below the pressure at which the effluent stream leaves the OTO reactor and above atmospheric pressure, and in still another aspect it is less than 10 psi (69 kPa) below the pressure at which the effluent stream leaves the OTO reactor and above atmospheric pressure.

According to one embodiment of the present invention, a quench tower is employed as a quench device. In a quench tower, the effluent stream is intimately contacted (i.e., directly exposed in a common volume, and not separated by walls as described above for a heat exchanger) with a quench medium in the liquid state. The quench medium is introduced to the quench tower at a temperature that is both below the quench medium bubble point temperature and the gaseous effluent stream dew point temperature at the lowest pressure within the quench tower. The quench medium is introduced in sufficient volume to cause the effluent stream to move rapidly below its dew point temperature such that a substantial portion of the effluent stream rapidly condenses.

In one embodiment, the temperature of the quench medium is below the quench medium dew point temperature and the aqueous dew point temperature of the effluent stream at the lowest pressure in the quench tower, and causes a substantial portion of the water present in the effluent stream to condense. The quench medium, according to one method of use, is introduced into the quench tower at a location or locations above where the effluent stream is introduced, such that it will fall within the tower and be contacted with the effluent stream as it, or portions of it including the prime olefins in a gaseous state, rise through the tower. The quench tower typically includes internal elements to facilitate the intimate contacting of the quench medium with the reactor effluent or portions thereof, including liquid distributors and contacting devices such as baffles or trays. Intimate contacting with a liquid quench medium facilitates drawing catalyst fines out of the reactor effluent, into a free-flowing, dilute liquid phase and away from at least a portion of the prime olefins in a gaseous state. The quench tower usually also include other elements, such as heat exchangers used to cool the quench medium that is recirculated into the quench tower.

In a particular embodiment, the quench medium is water. In another embodiment, the quench medium is a portion of the water that has been recovered from the quench tower and cooled (thus reintroduced to the quench tower), and which contains at least a portion of the solids separated from the gaseous effluent stream. In one embodiment, the quench medium is a portion of the water that has been recovered from the bottom of the quench tower. For the purpose of this invention, the temperature of the quench medium is measured in the outlet of the quench device. The outlet temperature is a function of the composition of the liquid leaving the quench device and the pressure of the quench device as it will be at or below the bubble point of the composition. According to one embodiment, the quench medium has a temperature ranging from about 95° C. to about 120° C., preferably ranging from about 100° C. to about 115° C., preferably ranging from about 102° C. to about 110° C., preferably ranging from about 105° C. to about 110° C.

According to one embodiment, the quench is operated under conditions such that the cooled process gas then enters a quench tower where effluent water is condensed, acetic acid is neutralized and some heavy oxygenates (C3–C4+ aldehydes, ketones & alchols) are rejected. The effluent stream after the quench is defined as the olefin stream.

Initial Separation of the Olefin Stream

In one particular embodiment of the invention, the quenched olefin stream is further processed by compression. In another embodiment, the compression is multi-staged compression. Two, three four or more stages can be used with two or three stages being preferred. According to one embodiment, the step of separating occurs during or after the multistage compression. According to another embodiment, the step of separating occurs after the third stage of compression.

The initial step of separation separates the compressed reactor effluent into a heavy fraction and a remaining fraction. According to one embodiment, the heavy fraction comprises a majority of pentene and other components of the olefin stream that has a boiling point that is below or equal to the boiling point of pentene. In another embodiment the heavy fraction comprises a majority of butylene and other components of the effluent stream that has a boiling point greater than or equal to the boiling point of butylene.

In one embodiment, the remaining fraction that is provided comprises not greater than about 50 wt % dimethyl ether, preferably not greater than about 20 wt % dimethyl ether, more preferably not greater than about 10 wt % dimethyl ether, and most preferably not greater than about 5 wt % dimethyl ether. Of course, for dimethyl ether to be removed from the remaining fraction, some measurable about must be present. Desirably, the provided olefins stream will contain at least about 100 wppm dimethyl ether, preferably at least about 500 wppm dimethyl ether, and more preferably at least about 1,000 wppm dimethyl ether.

Prior to entering the distillation column for the fractionation step and optionally prior to entering a separation device such as a condensate stripper for the separation step, the olefin stream, of one embodiment, is compressed to a pressure of at least about 200 psig (1,480 kPa absolute), preferably, at a pressure ranging from about 200 psig (1,480 kPa absolute) to about 290 psig (2,100 kPa absolute), more preferably from about 250 psig (1,825 kPa absolute) to about 290 psig (2,100 kPa absolute).

According to one embodiment, the olefin stream in the last compression step under the foregoing temperature and pressure conditions is directed into a coalescor. The coalescor allows a three-phase separation, a gas phase, a liquid hydrocarbon phase and an aqueous phase. The aqueous phase is directed to a methanol concentrator to separate any dissolved methanol in the water from the wastewater, according to techniques known in the art. The remaining fraction is in a gaseous phase. It is directed optionally to a water extraction unit or to the distillation column. The gaseous phase is also referred to as the remaining fraction hereafter. The liquid phase is directed to a condensate stripper that is operated under conditions to produce a bottoms stream. The bottoms stream is hereafter referred to as the heavy fraction. The stripper reboiler is operated under conditions to minimize the amount of ethylene and propylene in the heavy fraction.

According to one embodiment, the temperature of heavy fraction leaving the reboiler ranges from 65° C. to 125° C., more preferably from 100° C. to 125° C., even more preferably from 115° C. to 125° C., and most preferably 120° C.

The overhead from the condensate stripper is combined with the olefin stream before the final stage of pressurization, cooling and condensation in the compression train. Thus, the final stage of pressurization, cooling and condensation function similar to the overhead condenser on a distillation column. The stripper unit combined with the compression train this way separates the olefin stream into a heavy fraction of the olefin stream and an remaining fraction that is then directed optionally to a water absorption column or to the distillation column inlet.

According to another embodiment, the fractionation step is done by a first distillation column and the separation step is done by a second distillation column. Thus, the second distillation column is upstream from the first distillation column. The second distillation column separates the olefin stream into a heavy fraction and a remaining fraction. The remaining fraction is directed optionally to a water absorption apparatus or alternatively to the inlet of the distillation column.

Absorption Dehydration

During or after multi-stage compression, the olefin stream can be washed using a water absorbent, as described above, if desired. This wash can mitigate problems related to gas hydration and/or separate water phase formation.

According to one embodiment, the water absorbent wash following the compression stage is preferred. According to another embodiment, the water absorbent wash follows the step of separating.

It is desirable that any water present in the remaining fraction of the olefin stream will be at a concentration such that free water formation (i.e., formation of a separate water phase) or gas hydration does not significantly impede the fractionation. Gas hydration results in the formation of a clathrate compound or other solid hydrates. Clathrate and other hydrate compounds are solids, and are essentially insoluble in water. Such compounds can cause significant problems if formed in a fractionation column. Avoiding clathrate or solid hydrate formation is particularly important when a distillation column having trays is used in the distillation column of the present invention. This is because a separate water phase formed in the trays will impede mass transfer and add extra weight to each tray. Avoiding clathrate or solid hydrate formation can be accomplished by increasing the overall pressure and therefore temperature of operation of the column.

However, when the overall temperature of the distillation column is increased, the smaller the difference between the temperature of the distillation column bottoms and the quench medium. This makes the heat exhcange between the quench medium and the distillation column bottoms less efficient. If the temperature differential is sufficiently low, the quench medium won't be able to meet the energy demands of the reboiler of the distillation column. Accordingly, the previous step of separating a heavy fraction from the remaining fraction of the olefin stream allows a greater temperature differential between the quench medium and the distillation column bottoms stream.

It is desirable in this invention that the remaining portion of the olefin stream contain not greater than about 15,000 wppm water. Preferably the remaining portion of the olefin stream contains not greater than about 10,000 wppm water, more preferably not greater than 5,000 wppm water, and most preferably not greater than about 1,000 wppm water.

It is not necessary in this invention that the olefin stream be completely dry. That is, the olefin stream can contain some water. The benefit of the olefin stream containing some amount of water is that additional and/or complex drying equipment will not be needed before separating the dimethyl ether and other byproducts having a boiling lower than or equal to dimethyl ether ("heavier byproducts") from the olefin stream. Preferably, according to one embodiment, the olefin stream contains at least about 10 wppm water, more preferably at least about 100 wppm water, and most preferably at least about 200 wppm water.

If an olefin stream contains an unacceptably high concentration of water, a sufficient amount of the water can be removed either prior to or during separation of the heavier byproduct using a water absorbent. Examples of water absorbents include alcohols, amines, amides, nitrites, heterocyclic nitrogen containing compounds, or a combination of any of the preceding. Either monohydric alcohols or polyhydric alcohols can be used as the alcohol absorbent. Specific examples of absorbents include methanol, ethanol, propanol, ethylene glycol, diethylene glycol, triethylene glycol, ethanolamine, diethanolamine, triethanolamine, hindered cyclic amines, acetonitrile, n-methylpyrrolidone, dimethyl formamide, and combinations thereof.

To obtain a substantial degree of effectiveness, the water absorbent should contain little non-water absorbing components. For example, the water absorbent should contain at least about 75 wt % water absorbing components. Desirably, the water absorbent contains at least about 90 wt %, preferably at least about 95 wt %, and most preferably at least about 98 wt % water absorbent.

When a water absorbent is used to reduce the concentration of water in the olefin stream prior to separation of the heavier byproduct, a wash type of process using a wash vessel can be used. In essence, a wash process is one in which the olefin stream is contacted with water absorbent such that a substantial amount of the water is removed, i.e., washed out, from the olefin stream. The amount of absorbent added to the wash vessel should be sufficient to substantially reduce free water formation (i.e., formation of a separate liquid phase), particularly in the vessel that the separation of the heavier byproduct from the olefin takes place. In an embodiment, it is desirable that water absorbent be added to the wash vessel at a mole ratio of absorbent compound to total olefin feedstock to the wash vessel of about 4:1 to about 1:5000. Preferably, the absorbent is added at a mole ratio of from about 4:1 to about 1:100, and more preferably from about 1:10 to about 1:50.

Although the olefin stream can come from any conventional source, the invention is particularly suited to removing heavier byproduct from olefin streams made from an oxygenate-to-olefin process. In one embodiment of this invention, an olefin stream containing dimethyl ether is obtained by contacting oxygenate feedstock with a molecular sieve catalyst.

In a preferred embodiment of the process of the invention, the oxygenate feedstock contains one or more oxygenates, more specifically, one or more organic compound(s) containing at least one oxygen atom. In a preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In a preferred embodiment, the feedstock is selected from one or more of methanol, ethanol, dimethyl ether, diethyl ether or a combination thereof, more preferably methanol and dimethyl ether, and most preferably methanol.

Fractionation

In one embodiment of this invention, the remaining fraction of the olefin stream is directed into a distillation column and is separated into a first fraction and a second fraction. The first fraction comprises a majority of ethylene and/or propylene. The second fraction comprises a majority of one or more heavier biproduct. The actual upper pressure limit of the separation process will typically depend upon the temperature at which the second fraction is separated. The second fraction will contain heavier byproducts as defined herein. It is desirable to keep the compounds in the second fraction sufficiently low in temperature so as not to cause chemical degradation or fouling problems in other downstream separation and treating equipment. In one embodiment, separation will be such that the second fraction will be at a temperature of not greater than about 250° C., preferably not greater than about 240° C., more preferably not greater than about 230° C.

In this invention, water absorbent, as described above, can optionally be added to the vessel in which the separation of the oxygenated byproducts from the olefin stream is performed. The addition of water absorbent directly to the separation vessel can be of additional beneficial in reducing free water and/or clathrate formation in the vessel.

In one embodiment of the invention, water absorbent is optionally added to the oxygenate separation vessel in an amount sufficient to substantially reduce clathrate formation. It is preferred that water absorbent be added to the vessel at a molar ratio of water absorbent to total olefin feedstock entering the separation vessel from about 4:1 to about 1:5000. Higher molar ratios of water absorbent to total olefin feed are desirable for reducing oxygenate content; preferably from about 4:1 to about 1:1; most preferably from about 3:1 to about 1.2:1, and most preferably from about 2.5:1 to about 1.5:1. Lower molar ratios of water absorbent to total olefin feeds are desirable for reducing clathrate formation. It is preferred that water absorbent be added to the vessel at a molar ratio of water absorbent to total olefin feedstock entering the separation vessel from about 1:1 to about 1:5,000, more preferably from about 1:100 to about 1:4000, and most preferably from about 1:500 to about 1:3000.

It is preferred that water absorbent be added to the vessel at a molar ratio of water absorbent to total olefin feedstock entering the separation vessel from about 4:1 to about 1:5000, more preferably from about 1:2 to about 1:50, and most preferably from about 1:5 to about 1:25.

In one embodiment of this invention, separation is by conventional distillation. Distillation is carried out using a vessel or tower having internal packing or trays that creates a temperature difference from top to bottom of the tower. The upper portion of the tower is the cooler portion, and higher volatile components in the feedstock exit from the top of the tower.

In this invention it is desirable to obtain high concentrations of ethylene and propylene from an olefin stream containing heavier byproduct. In one embodiment, the heavier byproduct is separated from the ethylene and propylene in the olefin stream. In this embodiment the ethylene and propylene are recovered in a first fraction, and the heavier byproduct is recovered in a second fraction. Typically, the first fraction will be the overhead or side fraction of a distillation column, and the second fraction will be a bottoms fraction or additional side fraction of a distillation column. When the first fraction and the second fraction are both side fractions, the components of the second fraction are a heavier fraction than the components of the first fraction.

In one embodiment of the invention, a majority of the ethylene and propylene in the remaining fraction will be separated in a first fraction and a majority of the heavier byproduct in the remaining fraction will be separated in a second fraction. Preferably, the first fraction will contain at least about 75% of the ethylene and propylene in the remaining fraction, more preferably at least about 85%, and most preferably at least about 95%.

In another embodiment, at least about 75% of the heavier byproduct in the remaining fraction will be separated out in the second fraction. Preferably, at least about 85% of the heavier byproduct in the remaining fraction will be separated out in the second fraction, more preferably at least about 95%, and most preferably at least about 99%.

A majority of the propane in the remaining fraction can be separated out in either the first or second fraction. If the majority of the propane is contained in the first fraction, then there will be less separation steps in the purification of the second fraction. However, according to one embodiment, there is slightly increased levels of heavier byproduct in the first fraction when a majority of the propane is in the first fraction. In this embodiment, at least about 60% of the propane in the remaining fraction, preferably at least about 70%, and more preferably at least about 80% will be in the first fraction, and the first fraction will contain not greater than about 50 wppm, preferably not greater than about 25 wppm, more preferably not greater than about 10 wppm heavier byproduct, and most preferably not greater than about 5 wppm heavier byproduct.

If a majority of the propane in the provided olefin stream is separated out in the second fraction, then the concentration of dimethyl ether in the first fraction will be significantly lower. In this embodiment, at least about 60% of the propane in the provided olefin stream, preferably at least about 70%, and more preferably at least about 80% will be in the second fraction, and the second fraction will contain not greater than about 25 wppm, preferably not greater than about 15 wppm, more preferably not greater than about 5 wppm ether, and most preferably not greater than about 1 wppm heavier byproduct.

In another embodiment of the invention, the second fraction will also contain some hydrocarbon compounds having four or more carbons. These compounds are also known as $C_4+$ components. The amount of $C_4+$ components in the second fraction can vary, particularly depending upon the amount of propane in the second fraction. For example the second fraction can contain from about 5 wt % to about 90 wt % $C_4+$ components. In one embodiment, the second fraction contains from about 25 wt % to about 80 wt % of $C_4+$ components, more preferably from about 35 wt % to about 75 wt % of $C_4+$ components.

It is of further advantage in this invention to operate the distillation column at a temperature and pressure to separate out of the olefin stream at least a majority (i.e., at least 50%) of any propadiene which might be present. In this embodiment, the propadiene would preferably be separated out in the second fraction along with dimethyl ether. Preferably, at least about 75%, more preferably at least about 85%, and most preferably at least about 95% of the propadiene would be separated out. Separating out any propadiene out in this manner would necessarily include separating out a substantial portion of any methyl acetylene that is at times present in the olefin stream. This is because methyl acetylene has a lower normal boiling point than propadiene and dimethyl ether. Removing propadiene and methyl acetylene from the olefin stream would provide a substantial benefit in that the first fraction containing the ethylene and/or propylene would have a very high concentration of mono-olefin compounds. Such a stream would need little if any hydro processing, which might typically be needed to reduce the number of diolefins or alkylene compounds recovered in the first fraction.

It is an important feature of the present invention that the distillation is heat integrated to improve efficiency. In particular, the reboiler on the bottoms of the distillation column is heated with water from the quench stream. When the distillation column is operated at high pressures as described above, the corresponding temperature of the remaining fraction of the olefin stream is higher than it would have been had the pressure not been increased. The hotter the bottoms temperature, the less the difference between the quench water and the reboiler. Decreasing the pressure will decrease the respective bottoms temperature but will increase the likelihood of clathrate formation. However, because the step of separating occurs as previously described, the composition is separated into a heavy fraction and a remaining fraction. The removal of heavy components serves to reduce the distillation column bottoms temperature without having to reduce pressure.

In one embodiment, the quench medium and the distillation column bottoms respectively have a first and second temperature and the difference between the first temperature and the second temperature is at least about 10° C. In another embodiment, the difference between the first temperature and the second temperature is at least about 15° C. In yet another embodiment, the difference between the first temperature and the second temperature is at least about 20° C.

Caustic and Drying

This invention is particularly advantageous for treating the ethylene and propylene streams contained in the first fraction to remove entrained acid gases such as $CO_2$, which optionally can be present in such fraction. The advantage is that in this invention the separated ethylene and propylene streams will contain relatively few hydrocarbon components that cause fouling problems in such acid gas treatment systems.

Solid or liquid acid gas treatment systems can be used in this invention. In either system, the acid gas is removed from the ethylene and/or propylene stream in the first fraction by contacting the first fraction with an acid gas absorbent or adsorbent. Examples of such absorbents or adsorbents include amines, potassium carbonate, caustic, alumina, molecular sieves, and membranes, particularly membranes formed of polysulfone, polyimid, polyamide, glassy polymer and cellulose acetate. Solutions containing amines and caustic compounds are preferred, with caustic compounds being more preferred.

Aqueous amine solutions which are useful in this invention can contain any amine compound or compounds suitable for acid gas absorption. Examples include alkanolamines, such as triethanolamine (TEA); methyldiethanolamine (MDEA); diethanolamine (DEA); monoethanolamine (MEA); diisopropanolamine (DIPA); and hydroxyaminoethyl ether (DGA). Effective concentrations can range from about 0.5 to about 8 moles of amine per liter of aqueous solution.

Piperazine and/or monomethylethanolamine (MMEA) can be added to aqueous amine solutions to enhance their absorption capabilities. These additives can be included in the aqueous solution at a concentration of from about 0.04 to about 2 moles per liter of aqueous solution.

Caustic compounds which can be used in this invention are alkaline compounds which are effective in removing acid gas from an olefin stream. Examples of such alkaline compounds include sodium hydroxide and potassium hydroxide.

Following acid gas treating, it is desirable to remove additionally entrained material in the treated ethylene and/or propylene using a water wash. Conventional equipment can be used. It is desirable, however, to further remove additional water from the separated ethylene and/or propylene streams.

In one embodiment of the invention, the ethylene and propylene in the first fraction is water washed, i.e., contacted with a water stream, prior to acid gas treating. This contacting is particularly advantageous when water absorbent is added to the oxygenate separation vessel, as water absorbent is likely to carry over into the first or overhead fraction. Water washing would then be conducted to remove a substantial portion of water absorbent carry over prior to acid gas treating.

This invention further includes an optional drying embodiment. In this embodiment, a solid or liquid drying system can be used to remove water and/or additional oxygenated hydrocarbons from the first fraction.

In the solid drying system, the ethylene and/or propylene having been separated in a first fraction, and optionally acid gas treated and water washed, is contacted with a solid adsorbent to further remove water and oxygenated hydrocarbon to very low levels. Typically, the adsorption process is carried out in one or more fixed beds containing a suitable solid adsorbent.

Adsorption is useful for removing water and oxygenated hydrocarbons to very low concentrations, and for removing oxygenated hydrocarbons that normally is not removed by using other treatment systems. Preferably, an adsorbent system used as part of this invention has multiple adsorbent beds. Multiple beds allow for continuous separation without the need for shutting down the process to regenerate the solid adsorbent. For example, in a three bed system typically one bed is on-line, one bed is regenerated off-line, and a third bed is on stand-by.

The specific adsorbent solid or solids used in the adsorbent beds depends on the types of byproducts being removed. Examples of solid adsorbents for removing water and various polar organic compounds, such as oxygenated hydrocarbons and absorbent liquids, include aluminas, silica, 3A molecular sieves, 4A molecular sieves, and alumino-silicates. Beds containing mixtures of these sieves or multiple beds having different adsorbent solids can be used to remove water, as well as a variety of oxygenated hydrocarbons.

In this invention, one or more adsorption beds can be arranged in series or parallel. In one example of a series arrangement, a first bed is used to remove the smallest and most polar molecules which are the easiest to remove. Subsequent beds for removing larger less polar oxygenated species are next in series. As a specific example of one type of arrangement, water is first selectively removed using a 3A molecular sieve. This bed is then followed by one or more beds containing one or more less selective adsorbents such as a larger pore molecular sieve e.g. 13× and/or a high surface area active alumina such as Selexorb CD (Alcoa tradename).

In another embodiment, the first bed is a 3.6A molecular sieve capable of selectively removing both water and methanol. This bed can then be followed by one or more 13× or active alumina beds as described above.

The adsorbent beds can be operated at ambient temperature or at elevated temperature as required, and with either upward or downward flow. Regeneration of the adsorbent materials can be carried out by conventional methods including treatment with a stream of a dry inert gas such as nitrogen at elevated temperature.

In the liquid drying system, a water absorbent is used to remove water from the first fraction. The water absorbent can be any liquid effective in removing water from an olefin stream. Preferably the water absorbent is the same as previously described. Preferably the olefin from the adsorption beds contains less than about 100 wppm water, more preferably less than about 10 wppm, and most preferably less than 1 wppm. Preferably less than about 10 wppm dimethyl ether is present in the stream leaving the adsorption beds, more preferably less than about 5 wppm, and most preferably less than about 1 wppm.

Isolating Propylene and Ethylene Streams

Following drying, the gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a dethanizer, a wash tower often referred to as a caustic wash tower and/or quench tower, absorbers, adsorbers, membranes, ethylene (C2) splitter, propylene (C3) splitter, and the like.

Various recovery systems useful for recovering predominately olefin(s), preferably prime or light olefin(s) such as ethylene, propylene and/or butylene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, byproducts and/or contaminants along with the preferred prime products. The preferred prime products, the light olefins, such as ethylene and propylene, are typically purified for use in derivative manufacturing processes such as polymerization processes. Therefore, in a preferred embodiment of the recovery system, the recovery system also includes a purification system. For example, the light olefin(s) produced particularly in a oxygenate to olefin process are passed through a purification system that removes low levels of byproducts or contaminants.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application No. 09/689,363 filed Oct. 20, 2000 (purge stream using hydrating catalyst), which is herein incorporated by reference.

In one embodiment, the effluent gas withdrawn from the reactor is passed through a recovery system producing one or more hydrocarbon containing stream(s), in particular, a three or more carbon atom ($C_3^+$) hydrocarbon containing stream. In this embodiment, the $C_3^+$ hydrocarbon containing stream is passed through a first fractionation zone producing a crude $C_3$ hydrocarbon and a $C_4^+$ hydrocarbon containing stream, the $C_4^+$ hydrocarbon containing stream is passed through a second fractionation zone producing a crude $C_4$ hydrocarbon and a $C_5^+$ hydrocarbon containing stream. The four or more carbon hydrocarbons include butenes such as butene-1 and butene-2, butadienes, saturated butanes, and isobutanes.

Polymerization

The ethylene and propylene streams treated and separated according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, chromium oxide and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives are alternatively formed from the ethylene, propylene and $C_4^+$ olefins, particularly butylene, separated according to this invention. The olefins separated according to this invention can also be used in the manufacture of such compounds as aldehydes, acids such as $C_2$–$C_{13}$ mono carboxylic acids, alcohols such as $C_2$–$C_{12}$ mono alcohols, esters made from the $C_2$–$C_{12}$ mono carboxylic acids and the $C_2$–$C_{12}$ mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4$+ olefins, butylene in particular, are particularly suited for the manufacture of aldehydes, acids, alcohols, esters made from $C_5$–$C_{13}$ mono carboxylic acids and $C_5$–$C_{13}$ mono alcohols and linear alpha olefins.

Figure 1:
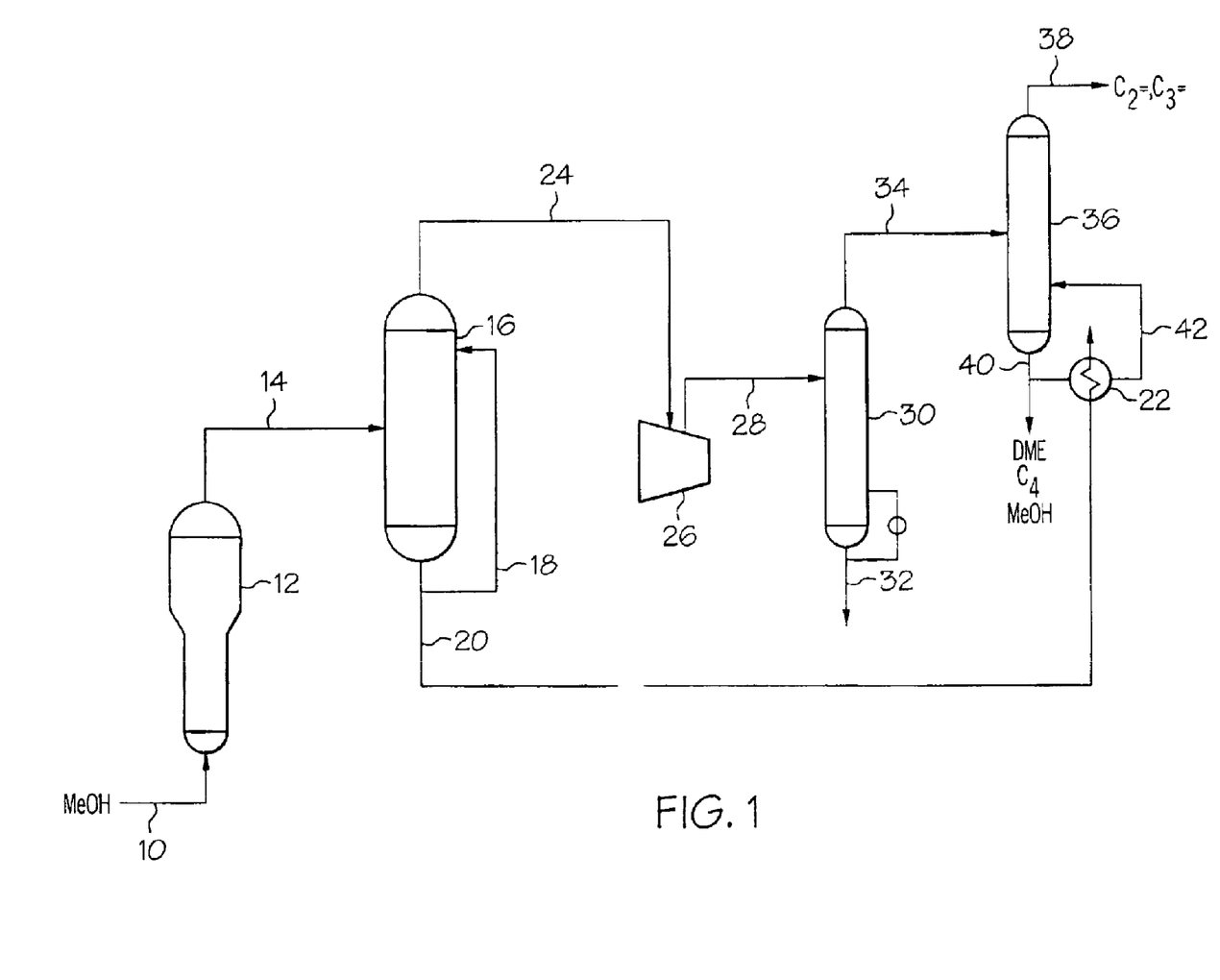
FIG. 1 is a flow diagram showing one embodiment of a process for separating ethylene and propylene from other byproducts in a heat-integrated process.

FIG. 1 shows a flow scheme of the heat-integrated process of one embodiment of the present invention. The methanol feedstream 10 is fed into an oxygenate to olefin reactor 12 and produces an olefin stream 14 containing olefins, water, methanol and byproducts. The effluent stream is cooled by direct contact in a quench tower 16. Particularly, water in the effluent stream is condensed by contact with the cooled quench stream 18. The condensed water from the effluent stream is removed from the bottom of the quench tower in a quench stream 20. A portion of the quench stream 20 is cooled and recycled in quench recycle stream 18. According to one embodiment, the remaining quench stream 20 is directed to a heat exchanger/reboiler 22.

The quenched effluent is removed from the overhead stream 24 of the quench tower 16 forming an olefin stream (also 24). The olefin stream is compressed by a compression train 26. The pressurized olefin stream 28 is then directed to a separating column 30. The separating column of one embodiment is a distillation column. The separating column of another embodiment is a condensate stripper. A heavy fraction 32 is removed in a bottoms stream (also 32) from the separating column. The heavy fraction, in one embodiment, comprises at least a majority of pentene and compounds having a boiling point below or equal to the boiling point of pentene. The remaining fraction of the olefin stream separating column separates the pressurized olefin stream into a remaining fraction 34 removed from the separating column in an overhead stream (also 34).

The remaining fraction 34 is optionally washed in a water extractant (not shown). It also optionally pressurized again (not shown). Then the remaining fraction of the olefin stream is directed to the distillation column 36. At least a majority of the ethylene and propylene is removed in the first fraction through the distillation column overhead 38. At least a majority of the heavier byproduct is removed from the distillation column bottoms 40. In one embodiment, the distillation column operates as a C3 splitter. In another embodiment, the distillation column operates as a depropanizer and removes at least a majority of the propylene.

A portion of the distillation column bottoms 40 forms a bottoms recycle stream 42 and passes through a heat exchanger/reboiler 22. A hot quench stream 20 from the quench tower 16 is used to boil the bottoms recycle stream. Because the separating column 30 removes the heavy fraction, there is a greater temperature difference between temperature of the bottoms stream and the temperature of the quench tower assuming all other conditions remain the same. The heat exchanger between the quench stream and the bottoms recycle stream has a greater temperature difference than if the olefin stream had not been separated into a heavy fraction and a remaining fraction.

Figure 2:
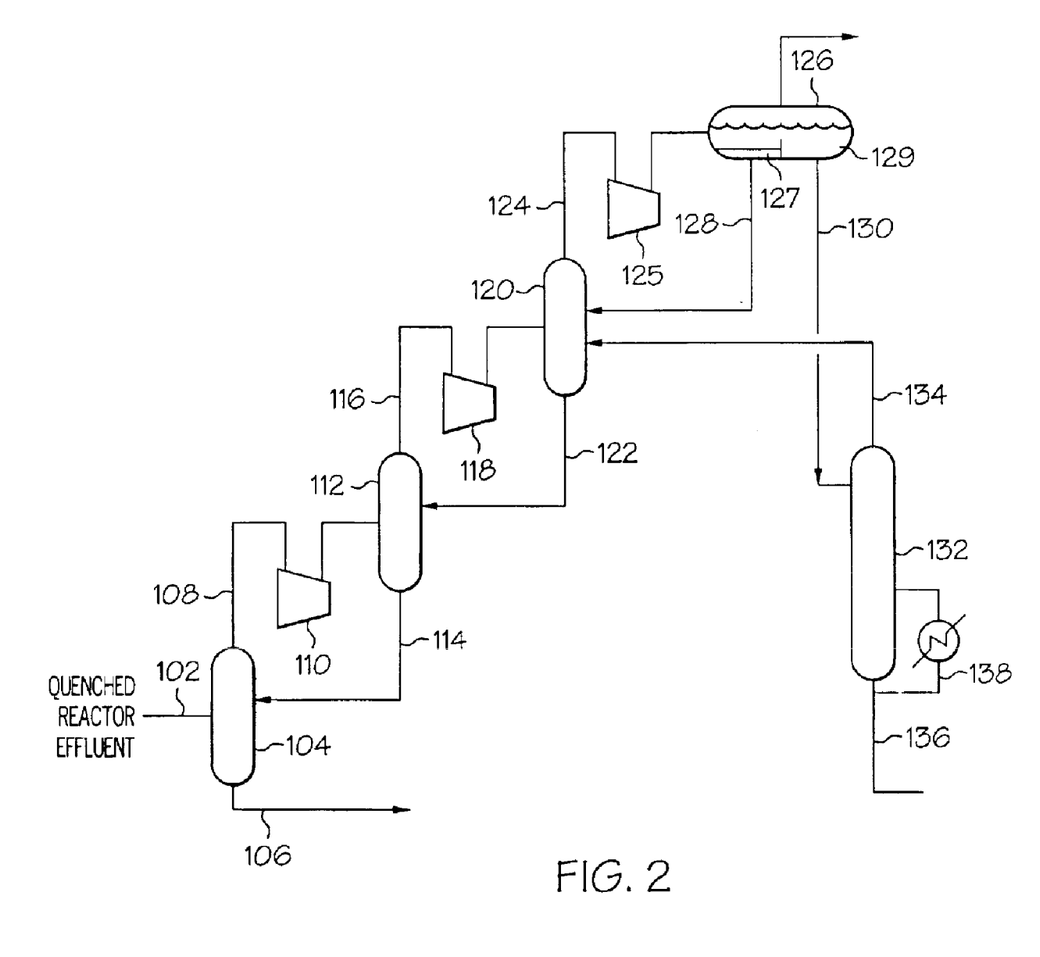
FIG. 2 is a flow diagram showing the pressurization and separation step of one embodiment of the present invention.

FIG. 2 describes a particular embodiment of the separation step of the present invention. The separation step comprises a three staged compression with a stripper to compress and separate the olefin stream into a heavy hydrocarbon fraction and a remaining fraction. Quenched reactor effluent forming an olefin stream 102 comes from the quench tower (not shown). The olefin stream is fed into a first knockout drum 104. Condensate (predominantly water and methanol) is removed through a first condensate stream 106. Gaseous effluent passes through the first knockout drum through the first vapor stream 108 to the first compressor 110. The effluent stream is compressed and optionally cooled with a heat exchanger (not shown). The effluent in the first vapor stream is conveyed to a second knockout drum 112.

The second knockout drum 112 collects the liquid condensate and removes it through a second condensate stream 114 (predominantly water and methanol) and returns it to the first knockout drum 104. The gas phase leaves the second knockout drum through the second vapor stream 116. The second vapor stream passes through the second compressor 118. The effluent is further compressed and optionally cooled in a heat exchanger (not shown). The effluent in the second vapor stream is conveyed to the third knockout drum 120.

The third knockout drum 120 collects the liquid condensate and removes it through a third condensate stream 122 (predominantly water and methanol) and returns it to the second knockout drum 112. The gas phase leaves the second knockout drum through a third vapor stream 124. The third vapor stream passes through a third compressor 125. The effluent is further compressed and cooled in a heat exchanger (not shown). The effluent in the third vapor stream is conveyed to a coalesceor 126.

The coalescor 126 separates the condensate into an aqueous condensate fraction 127 and a hydrocarbon condensate fraction 129. The aqueous condensate fraction comprises predominantly water and methanol and is removed from the coalescor through the fourth condensate stream 128. The hydrocarbon condensate fraction comprises primarily pentene and heavier hydrocarbons. The hydrocarbon condensate fraction is removed through the hydrocarbon condensate stream 130 and is fed into a condensate stripper 132. The condensate stripper separates the hydrocarbon stream into a stripper overhead stream 134 and a stripper bottoms stream 136. The stripper bottoms stream comprises the heavy hydrocarbon fraction as set forth in one or more embodiments above. A portion of the heavy fraction is reboiled and returned to the stripper in the stripper bottoms return 138.

The stripper overhead stream is fed into the third knockout drum 120 where it mixes with the effluent stream and is compressed in the third compressor 126 cooled in a heat exchanger (not shown) and fed into the coalescor 126. The hydrocarbon condensate stream from the coalescor recycles the hydrocarbon condensate back to the stripper. The gaseous phase of the effluent stream in the coalescor forms the remaining fraction as previously described in one or more of the embodiments above. The remaining fraction is removed from the coalescor and fed into the distillation column. Optionally, the remaining fraction can be sent to a water absorption column or subject to an additional step of pressurization before being sent to the distillation column.

Having now fully described this invention, it will be appreciated by those skilled in the art that the invention can be performed within a wide range of parameters within what is claimed, without departing from the spirit and scope of the invention.

What is claimed is:

1. A process for obtaining an ethylene and propylene enriched stream from an oxygenate to olefin reactor, the process comprising:
   a) providing an effluent stream from an oxygenate to olefins reactor comprising ethylene, propylene, dimethyl ether and one or more byproducts selected from the group consisting of propane, methyl acetylene, propadiene, acetaldyhde and butylene;
   b) quenching the effluent stream with a quench medium to provide an olefin stream;
   c) separating the olefin stream into a heavy fraction comprising C5+ olefins and a remaining fraction; and
   d) fractionating the remaining fraction in a distillation column to provide a first fraction comprising a majority of the ethylene and propylene and a second fraction comprising a majority of the dimethyl ether and a majority of a second compound selected from the group consisting of propadiene, methyl acetylene, and acetaldehyde, wherein a portion of the second fraction is heated by the quench medium.

2. The process for claim 1, wherein the quench medium has a temperature ranging from about 95° C. to about 120° C.

3. The process for claim 1, wherein the quench medium has a temperature ranging from about 100° C. to about 115° C.

4. The process for claim 1, wherein the quench medium has a temperature ranging from about 102° C. to about 110° C.

5. The process for claim 1, wherein the quench medium has a temperature ranging from about 105° C. to about 110° C.

6. The process for claim 1, wherein the quench medium has a temperature below 108° C. under adiabatic conditions.

7. The process far claim 1, wherein the quench medium and the second fraction respectively have a first and second temperature and the difference between the first temperature and the second temperature is at least about 10° C.

8. The process for claim 7, wherein the difference between the first temperature and the second temperature is at least about 15° C.

9. The process for claim 7, wherein the difference between the first temperature and the second temperature is at least about 20° C.

10. The process for claim 1, wherein the effluent strain contains from 50 wt % to 95 wt % ethylene excluding water.

11. The process for claim 1, wherein the effluent stream contains from 25 wt % to 75 wt % ethylene excluding water.

12. The process for claim 1, wherein the effluent stream contains from 25 wt % to 75 wt % ethylene excluding water.

13. The process for claim 1, wherein the effluent stream comprises from about 5 w % to 25 wt % of all components having a boiling point lower than the boiling point of dimethyl ether, excluding water.

14. The process for claim 1, wherein the effluent stream comprises from about 10 wt % to 20 wt % of all components having a boiling point lower than the boiling point of dimethyl ether, excluding water.

15. The process for claim 1, wherein the effluent stream comprises from about 12 wt % to 17 wt % of all components having a boiling point lower than the boiling point of dimethyl ether, excluding water.

16. The process for claim 1, wherein the heavy components comprises at least 25% of all components having a boiling point of or below the boiling point of pentene.

17. The process for claim 1, wherein the heavy components comprises at least 35% of all components having a boiling point of or below the boiling point of pentene.

18. The process for claim 1, wherein the heavy components comprises at least a majority of all components having a boiling point of or below the boiling point of pentene.

19. The process for claim 1, wherein the heavy components comprises at least 70% of all components having a boiling point of or below the boiling point of pentene.

20. The process for claim 1, wherein the heavy components comprises at least 90% of all components having a boiling point of or below the boiling point of pentene.

21. The process for claim 1, wherein the heavy components comprises at least 95% of all components having a boiling point of or below the boiling point of pentene.

22. The process for claim 1, wherein no more than about 10 wt % of the total weight of propylene and ethylene is present in the heavy fraction.

23. The process for claim 1, wherein no more than about 5 wt % of the total weight of propylene and ethylene is present in the heavy fraction.

24. The process for claim 1, wherein no more than about 2 wt % of the total weight of propylene and ethylene is present in the heavy fraction.

25. The process for claim 1, wherein no more than about 1 wt % of the total weight of propylene end ethylene is present in the heavy fraction.

26. The process for claim 1, wherein no more than about 0.5 wt % of the total weight of propylene and ethylene is present in the heavy fraction.

27. The process for claim 1, wherein the separating step is done with a condensate stripper.

28. The process for claim 1, wherein the fractionating step is done with a first distillation column and the separating step is done with a second distillation column.

29. The process for claim 1, wherein from 10 to 5,000 wppm of water enters the distillation column.

30. The process for claim 1, wherein the distillation column has an inlet and the pressure at the inlet of the distillation column is from 200 to 290 psig.

31. The process for claim 1, wherein the distillation column has an inlet and the pressure at to inlet of the distillation column is from 250 to 290 psig.

32. The process for claim 1, wherein water absorbent is added to the distillation column.

33. The process for claim 1, further comprising separating the ethylene and propylene in the first fraction and polymerizing the ethylene.

34. The process for claim 1, further comprising separating the ethylene and propylene in the first fraction and polymerizing the propylene.

35. The process for claim 1, wherein the temperature of the heavy fraction ranges from 65° C. to 125° C.

36. The process for claim 1, wherein the temperature of the heavy fraction ranges from 100° C. to 129° C.

37. The process for claim 1, wherein the temperature of the heavy fraction ranges from 115° C. to 125° C.

38. The process for claim 1, wherein the process further comprises:
   (e) substantially drying the first fraction to produce the ethylene and propylene enriched stream.

* * * * *